United States Patent [19]

Matsuo et al.

[11] Patent Number: 5,468,731
[45] Date of Patent: Nov. 21, 1995

[54] PEPTIDE COMPOUNDS, A PROCESS FOR PREPARATION THEREOF AND PHARMACEUTICAL COMPOSITION COMPRISING THE SAME

[75] Inventors: Masaaki Matsuo, Toyonaka; Daijiro Hagiwara, Moriguchi; Hiroshi Miyake, Kyoto, both of Japan

[73] Assignee: Fujisawa Pharmaceutical Co., Ltd., Osaka, Japan

[21] Appl. No.: 266,793

[22] Filed: Jun. 28, 1994

Related U.S. Application Data

[63] Continuation of Ser. No. 193,873, Feb. 8, 1994, abandoned, which is a continuation of Ser. No. 947,983, Sep. 21, 1992, abandoned, which is a continuation of Ser. No. 819,678, Jan. 13, 1992, abandoned, which is a continuation of Ser. No. 629,645, Dec. 7, 1990, abandoned.

[30] Foreign Application Priority Data

Dec. 22, 1989 [GB] United Kingdom ............. 8929070

[51] Int. Cl.$^6$ .................. A61K 38/00; C07K 5/00; C07K 7/00; C07K 17/00
[52] U.S. Cl. .................. 514/18; 514/19; 530/331; 530/332; 562/575; 548/535; 548/532
[58] Field of Search ................. 562/575; 548/535, 548/532; 530/331, 332; 514/18, 19

[56] References Cited

U.S. PATENT DOCUMENTS

| | | | |
|---|---|---|---|
| 4,223,020 | 9/1980 | Momany | 514/18 |
| 5,321,032 | 6/1994 | Matsuo et al. | 514/308 |

FOREIGN PATENT DOCUMENTS

| | | |
|---|---|---|
| 0074787 | 3/1983 | European Pat. Off. |
| 0333174 | 9/1989 | European Pat. Off. |

OTHER PUBLICATIONS

Life Science, vol. 31, 1982, pp. 2249–2252, R. J. Vavrek, et al., "Selectivity of Minimum Structure Enkepholins". Dipeptides and Amino Acids, vol. 2, 1983, pp. 369–370.

A. Ljungqvist et al., Increased Potency of Antagonists of Substances P having Asparagine in Position 6, Regulatory Peptides, vol. 24, No. 3, Mar. 1989, pp. 283–291.

Primary Examiner—Jill Warden
Assistant Examiner—Sheela J. Huff
Attorney, Agent, or Firm—Oblon, Spivak, McClelland, Maier & Neustadt

[57] ABSTRACT

A compound of the formula:

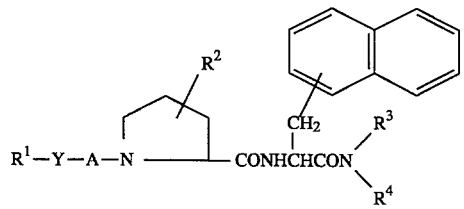

wherein
$R^1$ is aryl, or a group of the formula:

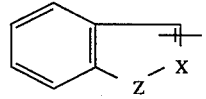

wherein
X is CH or N, and Z is O or N—$R^5$, in which $R^5$ is hydrogen or lower alkyl,
$R^2$ is hydroxy or lower alkoxy,
$R^3$ is hydrogen or lower alkyl which may have suitable substituent(s),
$R^4$ is ar(lower)alkyl which may have suitable substituent(s),
A is carbonyl or sulfonyl, and
Y is a bond or lower alkenylene,
and pharmaceutically acceptable salt thereof. The disclosed compounds are useful for treating respiratory diseases such as bronchaedema.

10 Claims, No Drawings

PEPTIDE COMPOUNDS, A PROCESS FOR PREPARATION THEREOF AND PHARMACEUTICAL COMPOSITION COMPRISING THE SAME

This application is a continuation of application Ser. No. 08/193,873 filed Feb. 8, 1994, now abandoned, which is a continuation of application Ser. No. 07/947,983 filed Sep. 21, 1992, now abandoned which is a continuation of Ser. No. 07/819,678 filed Jan. 13, 1992, now abandoned, which is a continuation of Ser. No. 07/629,645 filed Dec. 7, 1990, now abandoned.

The present invention relates to new peptide compounds and pharmaceutically acceptable salts thereof.

More particularly, it relates to new peptide compounds and pharmaceutically acceptable salts thereof which have pharmacological activities such as tachykinin antagonism, especially substance P antagonism, neurokinin A antagonism, neurokinin B antagonism, and the like, to a process for preparation thereof, to pharmaceutical composition comprising the same, and to a use of the same as a medicament.

One object of the present invention is to provide new and useful peptide compounds and pharmaceutically acceptable salts thereof which have pharmacological activities such as tachykinin antagonism, especially substance P antogonism, neurokinin A antagonism, neurokinin B antagonism, and the like.

Another object of the present invention is to provide a process for the preparation of said peptide compounds and salts thereof.

A further object of the present invention is to provide a pharmaceutical composition comprising, as an active ingredient, said peptide compounds and pharmaceutically acceptable salts thereof.

Still further object of the present invention is to provide a use of said peptide compound or a pharmaceutically acceptable salt thereof as tachykinin antagonist, especially substance P antogonist, neurokinin A antagonist or neurokinin B antagonist, useful for treating or preventing tachykinin mediated diseases, for example, respiratory diseases such as asthma, bronchitis, rhinitis, cough, expectoration, and the like; opthalmic diseases such as conjunctivitis, vernal conjunctivitis, and the like; cutaneous diseases such as contact dermatitis, atopic dermatitis, urticaria, and other eczematoid dermatitis, and the like; inflammatory diseases such as rheumatoid arthritis, osteoarthritis, and the like; pains or aches (e.g., migraine, headache, toothache, cancerous pain, back pain, etc.); and the like in human being or animals.

The object compound of the present invention can be represented by the following general formula (I).

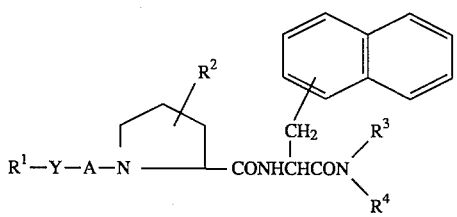

wherein

R$^1$ is aryl, or a group of the formula:

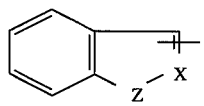

wherein

X is CH or N, and

Z is O or N—R$^5$, in which R$^5$ is hydrogen or lower alkyl,

R$^2$ is hydroxy or lower alkoxy,

R$^3$ is hydrogen lower alkyl which may have suitable substituent(s),

R$^4$ is ar(lower)alkyl which may have suitable substituent(s),

A is carbonyl or sulfonyl, and

Y is bond, or lower alkenylene.

According to the present invention, the new peptide compounds (I) can be prepared by processes which are illustrated in the following schemes.

Process 1

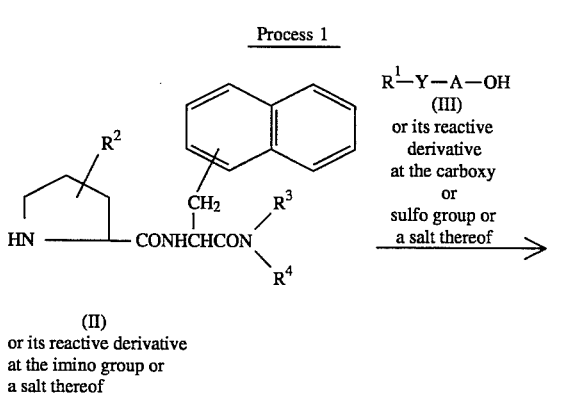

(II)
or its reactive derivative
at the imino group or
a salt thereof

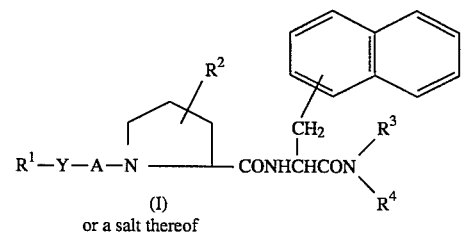

(I)
or a salt thereof

Process 2

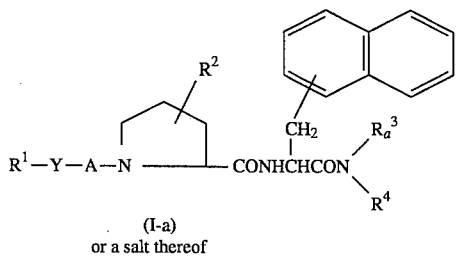

(I-a)
or a salt thereof

↓ Removal of the hydroxy protective group in R$_a^3$

-continued
Process 2

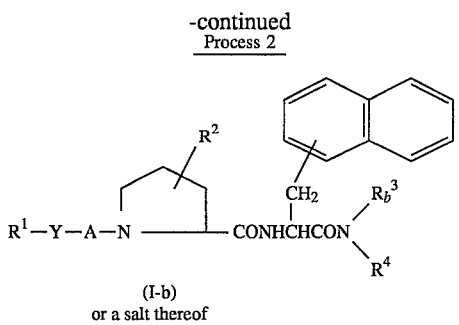

(I-b)
or a salt thereof wherein $R^1$, $R^2$, $R^3$, $R^4$, A and Y are each as defined above, $R_a^3$ is protected by hydrox (lower) alkyl, and $R_b^3$ is hydroxy (lower) alkyl.

As to the starting compound (II), it is novel and can be prepared by processes which are illustrated in the following schemes.

Process A

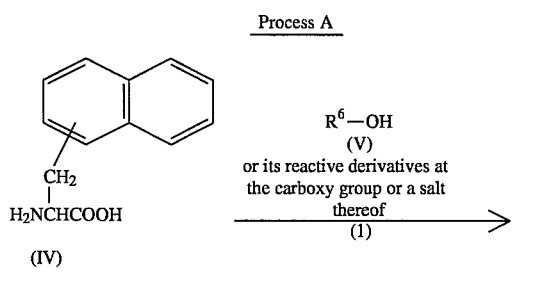

(IV)
or its reactive derivatives
at the amino group or
a salt thereof

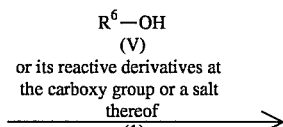

(VII)
or its reactive derivative
at the amino group
or a salt thereof
(2)

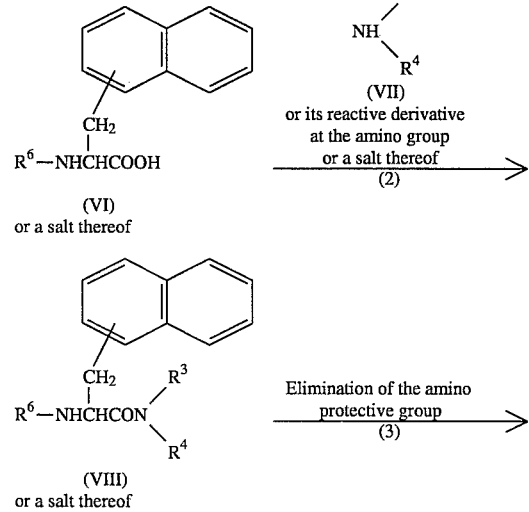

(VI)
or a salt thereof (VIII)
or a salt thereof

-continued
Process A

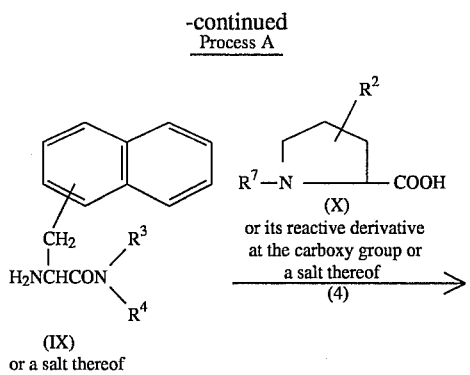

(IX)
or a salt thereof (X)
or its reactive derivative
at the carboxy group or
a salt thereof
(4)

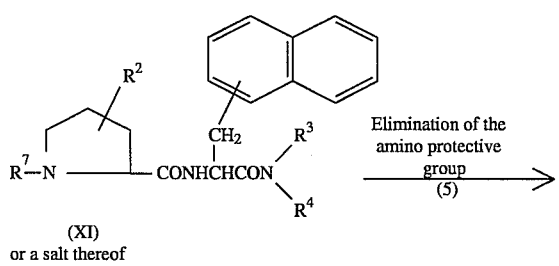

(XI)
or a salt thereof

Elimination of the
amino protective
group
(5)

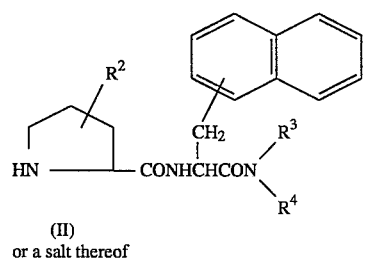

(II)
or a salt thereof wherein $R^2$, $R^3$ and $R^4$ are each as defined above, and $R^6$ and $R^7$ are each an amino protective group.

Throughout the present specification, the amino acid, peptides, protective groups, condensing agents, etc. are indicated by the abbreviations according to the IUPAC-IUB (Commission on Biological Nomenclature) which are in common use in the field of art.

Moreover, unless otherwise indicated, the amino acids and their residues when shown by such abbreviations are meant to be L-configured compounds and residues.

Suitable pharmaceutically acceptable salts of the starting and object compound are conventional non-toxic salt and include an acid addition salt such as an organic acid salt (e.g. acetate, trifluoroacetate, maleate, tartrate, methanesulfonate, benzenesulfonate, formate, toluenesulfonate, etc.), an inorganic acid salt (e.g. hydrochloride, hydrobromide, hydriodide, sulfate, nitrate, phosphate, etc.), or a salt with an amino acid (e.g. arginine, aspartic acid, glutamic acid, etc.), or a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), or the like.

In the above and subsequent descriptions of the present specification, suitable examples and illustrations of the various definitions which the present invention include within the scope thereof are explained in detail as follows.

The term "lower" is intended to mean 1 to 6, preferably 1 to 4 carbon atom(s), unless otherwise indicated.

Suitable "lower alkyl" may include a straight or branched one such as methyl, ethyl, propyl, isopropyl, butyl, isobutyl, tert-butyl, pentyl, hexyl, and the like, in which the most preferred one is methyl.

Suitable "aryl" may include phenyl, tolyl, xylyl, mesityl, cumenyt, naphtyl, and the like, in which the preferred one is $C_6$–$C_{10}$ aryl and the most preferred one is phenyl.

Suitable "lower alkenylene" is one having 2 to 6 carbon atom(s) and may include vinylene, propenylene, and the like, in which the preferred one is vinylene.

Suitable "lower alkyl which may have suitable substituent(s)" may include a conventional group, which is used in the field of art such as lower alkyl as exemplified above, carboxy(lower)alkyl (e.g. carboxymethyl, carboxyethyl, etc.), protected carboxy(lower)alkyl such as esterified carboxy(lower)alkyl, for example, lower alkoxycarbonyl(lower)alkyl (e.g. methoxycarbonytmethyl, ethoxycarbonylmethyl, methoxycarbonylethyl, etc.), carbamoyl(lower)alkyl which may have suitable substituent(s) such as carbamoyl(lower)alkyl (e.g., carbamoylmethyl, carbamoylethyl, carbamoylpropyl, etc.) and carbamoyl(lower)alkyl having suitable substituent(s), for example lower alkytcarbamoyl(lower)alkyl (e.g., methylcarbamoylmethyl, ethylcarbamoylmethyl, etc.), amino(lower)alkylcarbamoyl(lower)alkyl (e.g., aminomethylcarbamoylmethyl, aminoethylcarbamoylmethyl, etc.), lower alkylamino(lower)alkylcarbamoyl(lower)alkyl (e.g. dimethylaminomethylcarbamoylmethyl, dimethylaminoethylcarbamoylmethyl, etc.), lower alkylamino(lower)alkyl (e.g, dimethylaminomethyl, dimethylaminoethyl, etc.), hydroxy(lower)alkyl (e.g., hydroxymethyl, hydroxyethyl, etc), protected hydroxy(lower)alkyl such as acyloxy(lower)alkyl, for example, lower alkanoyloxy(lower)alkyl (e.g. acetyloxyethyl, acetyloxypropyl, acetyloxybutyl, acetyloxypentyl, propionyloxymethyl, butyryloxymethyl, hexanoyloxymethyl, etc.), and the like.

Suitable "ar(lower)alkyl which may have suitable substituent(s)" may include a conventional group, which is used in the field of amino acid and peptide chemistry, such as ar(lower)alkyl (e.g. trityl, benzhydryl, benzyl, phenethyl, etc.), substituted ar(lower)alkyl, for example, mono or di or trihalophenyl(lower)alkyl (e.g., o-fluorobenzyl, m-fluorobenzyl, p-fluorobenzyl, o-trifluoromethylbenzyl, etc.), and the like.

Suitable "amino protective group" may be a conventional protective group, which is used in the field of amino acid and peptide chemistry, that is, may include acyl such as lower alkanoyl (e.g. formyl, acetyl, propionyl, butyryl, isobutyryl, valeryl, isovaleryl, pivaloyl, hexanoyl, etc.), lower alkoxycarbonyl (e.g. methoxycarbonyl, ethoxycarbonyl, propoxycarbonyl, butoxycarbonyl, t-butoxycarbonyl, etc.), and the like.

Suitable "lower alkoxy" may include straight or branched one such as methoxy, ethoxy, propoxy, isopropoxy, butoxy, hexyloxy, and the like.

Suitable "hydroxy(lower)alkyl" and "protected hydroxy(lower)alkyl" may be the same as those exemplified above.

Particularly, the preferred embodiments of $R^1$, $R^2$, $R^3$, $R^4$, A and Y are as follows.

$R^1$ is phenyl; benzofuryl; indazolyl; or indolyl (e.g. 1H-indol-3-yl, etc.); 1-lower alkyl indolyl (e.g. 1-methyl-1H-indol-2-yl, 1-methyl-1H-indol-3-yl, 1-isopropyl-1H-indol-3-yl, etc.), $R^2$ is hydroxy; or lower alkoxy (e.g. methoxy, etc.), $R^3$ is hydrogen; lower alkyl (e.g. methyl, etc.); or hydroxy(lower)alkyl (e.g. hydroxymethyl, hydroxyethyl, etc.), $R^4$ is phenyl(lower)alkyl (e.g. benzyl, phenethyl, etc.); or halophenyl(lower)alkyl (e.g. o-fluorobenzyl, m-fluorobenzyl, p-fluorobenzyl, etc.), A is carbonyl; or sulfonyl, and Y is bond; or lower alkenylene (e.g. vinylene, etc.).

The processes for preparing the object compound (I) are explained in detail in the following.

Process 1

The object compound (I) or a salt thereof can be prepared by reacting the compound (II) or its reactive derivative at the imino group or a salt thereof with the compound (III) or its reactive derivative at the carboxy or sulfo group or a salt thereof.

Suitable reactive derivative at the imino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as bis(trimethylsilyl)acetamide, mono(trimethylsilyl)acetamide, bis(trimethylsilyl)urea or the like; a derivative formed by reaction of the compound (II) with phosphorus trichloride or phosgene, and the like.

Suitable salts of the compound (II) and its reactive derivative can be referred to the ones as exemplified for the compound (I).

Suitable reactive derivative at the carboxy or sulfo group of the compound (III) may include an acid halide, an acid anhydride, an activated amide, an activated ester, and the like. Suitable examples of the reactive derivatives may be an acid chloride; an acid azide; a mixed acid anhydride within acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid, [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminomethyl [$(CH_3)_2N^+$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from then according to the kind of the compound (III) to be used.

Suitable salts of the compound (III) and its reactive derivative may be a base salt such as an alkali metal salt [e.g. sodium salt, potassium salt, etc.], an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], or the like, and an acid addition salt as exemplified for the compound (I).

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (III) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethytaminopropyl)carbodiimide; N,N'-carbonylbis-(2-methylimidazole); pentamethyleneketene-N-cyclohexylimine; diphenylketene-N-cyclohexylimine, ethoxyacetylene; 1-alkoxy-1-chloroethylene, trialkyl phosphite; ethyl polyphosphate; isopropyl polyphosphate; phosphorus oxychloride (phosphoryl chloride); phosphorus trichloride; diphenyl phosphorylazide; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; benzotriazol-1 -yl-oxy-tris(dimethylamino)phosphoniumhexafluorophosphate; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to warming.

Process 2

The object compound (I-b) or a salt thereof can be prepared by subjecting the compound (I-a) or a salt thereof to removal reaction of the hydroxy protective group in $R_a^3$.

In the present removal reaction, all conventional methods used in the removal reaction of the hydroxy protective group, for example, hydrolysis, reduction, elimination using Lewis acid, etc. are applicable.

The processes for preparing the starting compound (II) are explained in detail in the following.

Process A

Process (1)

The compound (VI) or a salt thereof can be prepared by reacting the compound (IV) or its reactive derivatives at the amino group or a salt thereof with the compound (V) or its reactive derivative at the carboxy group or a salt thereof.

Suitable salts of the compound (V) can be referred to the ones as exemplified for the compound (III).

Suitable salts of the compound (VI) can be referred to the ones as exemplified for the compound (I).

This reaction can be carried out in substantially the same manner as Process 1, and therefore the reaction mode and reaction conditions [e.g. reactive derivatives, solvents, reaction temperature, etc.] of this reaction are to be referred to those as explained in Process 1.

Process (2)

The compound (VIII) or a salt thereof can be prepared by reacting the compound (VI) or a salt thereof with the compound (VII) or its reactive derivative at the amino group or a salt thereof.

Suitable salts of the compound (VII) can be referred to the ones as exemplified for the compound (II).

Suitable salts of the compound (VIII) can be referred to the ones as exemplified for the compound (I).

This reaction can be carried out in substantially the same manner as Process 1, and therefore the reaction mode and reaction conditions [e.g. reactive derivatives, solvents, reaction temperature, etc.] of this reaction are to be referred to those as explained in Process 1.

Process (3)

The compound (IX) or a salt thereof can be prepared by subjecting a compound (VIII) or a salt thereof to elimination reaction of the amino-protective group.

Suitable salts of the compounds (VIII) and (IX) can be referred to the ones as exemplified for the compound (I).

This reaction is carried out in accordance with a conventional method such as hydrolysis, reduction or the like.

The hydrolysis is preferably carried out in the presence of a base or an acid including Lewis acid.

Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, hydrazine, trialkylamine [e.g. trimethylamine, triethylamine, etc.], picoline, 1,5-diazabicyclo[4.3.0] -non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, sulfuric acid, hydrogen chloride, hydrogen bromide, hydrogen fluoride, etc.] and an acid additions salt compound [e.g. pyridine hydrochloride, etc.].

The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, chloroform, tetrachloromethane, tetrahydrofuran, a mixture thereof or any other solvent which does not adversely influence the reaction. A liquid base or acid can be also used as the solvent. The reaction temperature is not critical and the reaction is usually carried out under cooling to heating.

The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonte, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron etc.], copper catalysts [e.g. reduced copper, Raney copper, Ullman copper, etc.] and the like.

The reduction is usually carried out in a conventional solvent which does not adversely influence the reaction such as water, methanol, ethanol, propanol, N,N-dimethylformamide, or a mixture thereof. Additionally, in case that the above-mentioned acid to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to heating.

Process (4)

The compound (XI) or a salt thereof can be prepared by reacting the compound (IX) or a salt thereof with the compound (X) or its reactive derivative at the carboxy group or a salt thereof.

Suitable salts of the compound (X) can be referred to the ones as exemplified for the compound (III).

Suitable salts of the compound (XI) can be referred to the ones as exemplified for the compound (I).

This reaction can be carried out in substantially the same manner as Process 1, and therefore the reaction mode and reaction conditions [e.g. reactive derivatives, solvents, reaction temperature, etc.] of this reaction are to be referred to those as explained in Process 1.

Process (5)

The compound (II) or a salt thereof can be prepared by subjecting the compound (XI) or a salt thereof to elimination reaction of the amino protective group.

This reaction can be carried out in substantially the same manner as Process (3), and therefore the reaction mode and reaction conditions [e.g. bases, acids, reducing agents, catalysts, solvents, reaction temperature, etc.] of this reaction are to be referred to those as explained in Process (3).

The compounds obtained by the above processes can be isolated and purified by a conventional method such as pulverization, recrystallization, column chromatography, reprecipitation, or the like.

It is to be noted that the compound (I) and the other compounds may include one or more stereoisomers due to asymmetric carbon atoms, and all of such isomers and mixture thereof are included within the scope of this invention.

The object compounds (I) and pharmaceutically acceptable salt thereof have pharmacological activities such as tachykinin antagonism, especially substance P antagonism, neurokinin A antagonism or neurokinin B antagonism, and therefore are useful for treating or preventing tachykinin mediated diseases, particularly substance P mediated diseases, for example, respiratory diseases such as asthma, bronchitis, rhinitis, cough, expectoration, and the like; opthalmic diseases such as conjunctivitis, vernal conjunctivitis, and the like, cutaneous diseases such as contact dermatitis, atopic dermatitis, urticaria, and other eczematoid dermatitis, and the like; inflammatory diseases such as rheumatoid arthritis, osteoarthritis, and the like; pains or aches (e.g. migraine, headache, toothache, cancerous pain, back pain, etc.); and the like.

Further, it is expected that the object compound (I) of the present invention are useful for treating or preventing opthalmic diseases such as glaucoma, uveitis, and the like; gastrointestinal diseases such as ulcer, ulcerative colitis, irritable bowel syndrome, food allergy, and the like; inflammatory diseases such as nephritis, and the like; circulatory diseases such as hypertension, angina pectoris, cardiac failure, thrombosis, and the like; epilepsy; spastic paralysis; pollakiuria; dementia; Alzheimer's disease; schizophrenia; Huntington's chorea; carcinoid syndrome; and the like, and useful for immunosuppresive agent.

For therapeutic purpose, the compounds (I) and pharmaceutically acceptable salts thereof of the present invention can be used in a form of pharmaceutical preparation containing one of said compounds, as an active ingredient, in admixture with a pharmaceutically acceptable carrier such as an organic or inorganic solid or liquid excipient suitable for oral, parenteral, external or inhalant administration. The pharmaceutical preparations may be capsules, tablets, dragees, granules, solution, suspension, emulsion, or the like. If desired, there may be included in these preparation, auxiliary substances, stabilizing agents, wetting or emulsifying agents, buffers and other commonly used additives.

While the dosage of the compounds (I) will vary depending upon the age and condition of the patient, an average single dose of about 0.1 mg, 1 mg, 10 mg, 50 mg, 100 mg, 250 mg, 500 mg and 1000 mg of the compound (I) may be effective for treating asthma and the like. In general, amounts between 0.1 mg/body and about 1,000 mg/body may be administered per day.

In order to illustrate the usefulness of the object compound (I), the pharmacological test data of some representative compounds of the compound (I) are shown in the following.

Test Compounds

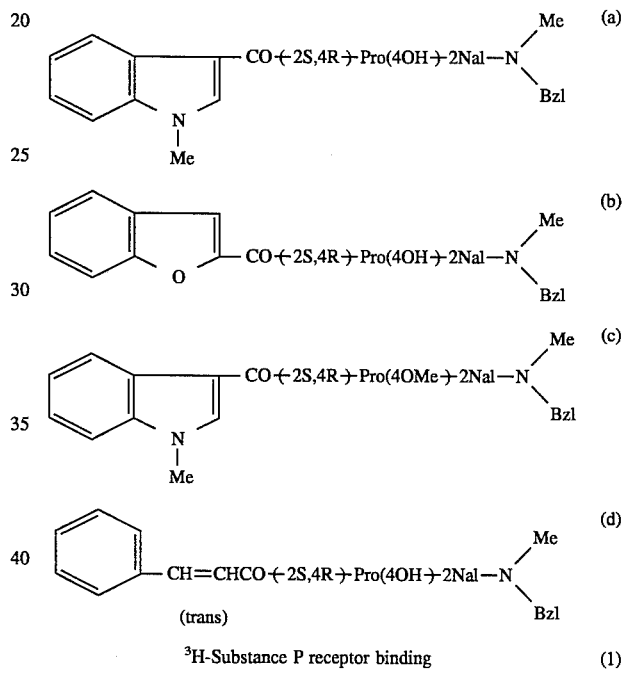

$^3$H-Substance P receptor binding (1)

Test Method:

(a) Crude lung membrane preparation

Male Hartley strain guinea pigs were sacrificed by decapitation. The trachea and lung were removed and homogenized in buffer (0.25M sucrose, 50 mM Tris-HCl pH 7.5, 0.1 mM EDTA) by using Polytoron (Kinematica). The homogenate was centrifuged (1000×g, 10 min) to remove tissue clumps and the supernatant was centrifuges (14000×g 20 min) to yield pellets. The pellets were resuspended in buffer (5 mM Tris-HCl pH 7.5), homogenized with a teflon homogenizer and centrifuged (14000×g, 20 min) to yield pellets which were referred to as crude membrane fractions. The obtained pallets were stored at $-70°$ C. until use.

(b) $^3$H-Substance P binding to preparation membrane

Frozen crude membrane fractions were thawed and resuspended in Medium 1 (50 mM Tris-HCl pH 7.5, 5 mM $MnCl_2$, 0.02% BSA, 2 µg/ml chymostatin, 4 µg/ml leupeptin, 40 µg/ml bacitracin.) $^3$H-substance P (1 nM) was incubated with 100 µl of the membrane preparation in Medium 1 at 4° C. for 30 minutes in a final volume of 500 µl. At the end of the incubation period, reaction mixture was quickly filtered over a Whatman GF/B glass filter (pretreated with 0.1% polyethylene imine for 3 hours prior to use) under aspiration. The filters were then washed four times with 5 ml of the buffer (50 mM Tris-HCl, pH 7.5). The radioactivity was counted in 5 ml of Aguazol-2 in Packerd scintillation counter (Packerd TRI-CARB 4530).
Test Results:

| Test Compounds (0.1 μl/ml) | Inhibition (%) |
|---|---|
| (a) | 96 |
| (b) | 94 |
| (c) | 100 |
| (d) | 96 |

(2) Effect of oral administration on substance P induced bronchoedema in guinea-pigs
Test Method:

Male Hartley guinea-pigs (300–400 g) were injected intravenously with Evans blue solution (20 mg/kg) containing Heparin (200 IU/kg) and substance P (10 n mol/kg). Each test compound (100 mg/kg) dissolved in dimethyl sulfoxide was orally given 30 minutes before this injection. After 10 minutes, the animals were sacrificed by bloodletting and the lungs were perfused with 50 ml of saline. Trachea and stem bronchi were dissected out and dissolved in 0.5 ml of 1N KOH solution at 37° C. for 6 hours. After the extraction with 4.5 ml of acetone-phosphate solution (0.6N $H_3PO_4$: acetone=5:13), the tissue Evans blue content was quantified colorimetrically at 620 nm.
Test Results:

| Test Compounds (100 mg/kg) | Inhibition (%) |
|---|---|
| (a) | 94 |
| (b) | 82 |
| (c) | 60 |
| (d) | 96 |

The following examples are given for purpose of illustrating the present invention in detail.

In these examples, there are employed the following abbreviations in addition to the abbreviations adopted by the IUPAC-IUB.

Ac: acetyl
Boc: t-butoxycarbonyl
BSA: bistrimethylsilylacetamide
Bzl: benzyl
Bzl(o-F): o-fluorobenzyl
Bzl(m-F): m-fluorobenzyl
Bzl(p-F): p-fluorobenzyl
HOBT: N-hydroxybenzotriazole
IPE: isopropyl ether
Me: methyl
1 Nal: 3-(1-naphthyl)alanine
2 Nal: 3-(2-naphthyl)alanine
NMM: N-methylmorpholine
4N-HCl/DOX: 4N-hydrogen chloride in 1,4-dioxane
Ph: phenyl
$Pr^i$: isopropyl
Pro(4OH): 4-hydroxyproline
Pro(4OMe): 4-methoxyproline
TEA: triethylamine
TFA: trifluoroacetic acid
THF: tetrahydrofuran
Tris-HCl: tris(hydroxymethyl)aminomethane hydrochloride
WSC: 1-ethyl-3-(3'-dimethylaminopropyl)carbodiimide The Starting Compounds used and the Object Compounds Obtained in the following Preparations and Examples are given in the Table as below, in which the formulae of the Starting Compounds are in the upper and the formulae of the Object Compounds are in the lower, respectively.

TABLE

| Preparation No. | Formula |
|---|---|
| 1 | H—2Nal—OH |
|   | Boc—2Nal—OH |
| 2 | Boc—2Nal—OH |
|   | Boc—2Nal—N(Me)(Bzl) |
| 3 | Boc—2Nal—N(Me)(Bzl) |
|   | HCl.H—2Nal—N(Me)(Bzl) |
| 4 | HCl.H—2Nal—N(Me)(Bzl) |
|   | Boc—(2S,4R)—Pro(4OH)—2Nal—N(Me)(Bzl) |

| | TABLE-continued | |
|---|---|---|
| 5 | Boc—(2S,4R)—Pro(4OH)—2Nal—N(Me)(Bzl) | |
| | HCl.H—(2S,4R)—Pro(4OH)—2Nal—N(Me)(Bzl) | |
| 6 | H—1Nal—OH | |
| | Boc—1Nal—OH | |
| 7-(1) | Boc—1Nal—OH | |
| | Boc—1Nal—N(Me)(Bzl) | |
| 7-(2) | Boc—2Nal—OH | |
| | Boc—2Nal—NHBzl | |
| 7-(3) | Boc—2Nal—OH | |
| | Boc—2Nal—N(Me)((CH$_2$)$_2$Ph) | |
| 7-(4) | Boc—2Nal—OH | |
| | Boc—2Nal—N(Me)(Bzl (m-F)) | |
| 7-(5) | Boc—2Nal—OH | |
| | Boc—2Nal—N(Me)(Bzl (o-F)) | |
| 7-(6) | Boc—2Nal—OH | |
| | Boc—2Nal—NH(CH$_2$)$_2$Ph | |
| 7-(7) | Boc—2Nal—OH | |
| | Boc—2Nal—N(Me)(Bzl (p-F)) | |
| 8 | Boc—2Nal—OH | |
| | Boc—2Nal—N((CH$_2$)$_2$OH)(Bzl) | |
| 9 | Boc—2Nal—N((CH$_2$)$_2$OH)(Bzl) | |
| | Boc—2Nal—N((CH$_2$)$_2$OAc)(Bzl) | |
| 10-(1) | Boc—1Nal—N(Me)(Bzl) | |
| | HCl.H—1Nal—N(Me)(Bzl) | |

TABLE-continued

| | |
|---|---|
| 10-(2) | Boc—2Nal—NHBzl<br>HCl.H—2Nal—NHBzl |
| 10-(3) | Boc—2Nal—N(Me)(CH₂)₂Ph<br>HCl.H—2Nal—N(Me)(CH₂)₂Ph |
| 10-(4) | Boc—2Nal—N(Me)Bzl(m-F)<br>HCl.H—2Nal—N(Me)Bzl(m-F) |
| 10-(5) | Boc—2Nal—N(Me)Bzl(o-F)<br>HCl.H—2Nal—N(Me)Bzl(o-F) |
| 10-(6) | Boc—2Nal—NH(CH₂)₂Ph<br>HCl.H—2Nal—NH(CH₂)₂Ph |
| 10-(7) | Boc—2Nal—N(Me)Bzl(p-F)<br>HCl.H—2Nal—N(Me)Bzl(p-F) |
| 10-(8) | Boc—2Nal—N((CH₂)₂OAc)Bzl<br>HCl.H—2Nal—N((CH₂)₂OAc)Bzl |
| 11-(1) | HCl.H—2Nal—N(Me)Bzl<br>Boc—(2S,4R)—Pro(4OMe)—2Nal—N(Me)Bzl |
| 11-(2) | HCl.H—1Nal—N(Me)Bzl<br>Boc—(2S,4R)—Pro(4OH)—1Nal—N(Me)Bzl |
| 11-(3) | HCl.H—2Nal—NHBzl<br>Boc—(2S,4R)—Pro(4OH)—2Nal—NHBzl |

TABLE-continued 11-(4)

HCl·H—2Nal—N(Me)(CH₂)₂Ph

Boc—(2S,4R)—Pro(4OH)—2Nal—N(Me)(CH₂)₂Ph 11-(5)

HCl·H—2Nal—N(Me)(Bzl(m-F))

Boc—(2S,4R)—Pro(4OH)—2Nal—N(Me)(Bzl(m-F))

11-(6)

HCl·H—2Nal—N(Me)(Bzl(o-F))

Boc—(2S,4R)—Pro(4OH)—2Nal—N(Me)(Bzl(o-F))

11-(7)

HCl·H — 2Nal — NH(CH₂)₂Ph
Boc — (2S,4R) — Pro(4OH) — 2Nal — NH(CH₂)₂Ph 11-(8)

HCl·H—2Nal—N(Me)(Bzl(p-F))

Boc—(2S,4R)—Pro(4OH)—2Nal—N(Me)(Bzl(p-F))

11-(9)

HCl·H—2Nal—N((CH₂)₂OAc)(Bzl)

Boc—(2S,4R)—Pro(4OH)—2Nal—N((CH₂)₂OAc)(Bzl)

12-(1)

Boc—(2S,4R)—Pro(4OH)—1Nal—N(Me)(Bzl)

HCl·H—(2S,4R)—Pro(4OH)—1Nal—N(Me)(Bzl)

12-(2)

Boc — (2S,4R) — Pro(4OH) — 2Nal — NHBzl
HCl·H — (2S,4R) — Pro(4OH) — 2Nal — NHBzl 12-(3)

Boc—(2S,4R)—Pro(4OH)—2Nal—N(Me)((CH₂)₂Ph)

HCl·H—(2S,4R)—Pro(4OH)—2Nal—N(Me)((CH₂)₂Ph)

TABLE-continued 12-(4)

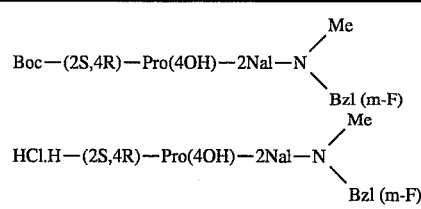

Boc—(2S,4R)—Pro(4OH)—2Nal—N(Me)(Bzl(m-F))

HCl.H—(2S,4R)—Pro(4OH)—2Nal—N(Me)(Bzl(m-F))

12-(5)

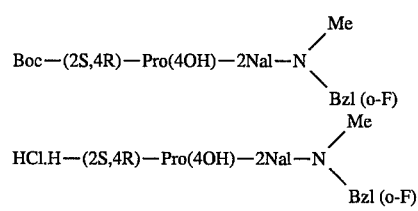

Boc—(2S,4R)—Pro(4OH)—2Nal—N(Me)(Bzl(o-F))

HCl.H—(2S,4R)—Pro(4OH)—2Nal—N(Me)(Bzl(o-F))

12-(6)

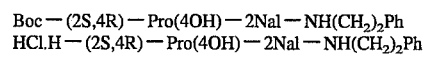

Boc—(2S,4R)—Pro(4OH)—2Nal—NH(CH$_2$)$_2$Ph
HCl.H—(2S,4R)—Pro(4OH)—2Nal—NH(CH$_2$)$_2$Ph 12-(7)

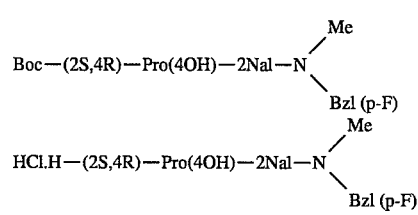

Boc—(2S,4R)—Pro(4OH)—2Nal—N(Me)(Bzl(p-F))

HCl.H—(2S,4R)—Pro(4OH)—2Nal—N(Me)(Bzl(p-F))

12-(8)

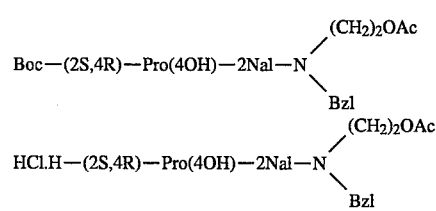

Boc—(2S,4R)—Pro(4OH)—2Nal—N((CH$_2$)$_2$OAc)(Bzl)

HCl.H—(2S,4R)—Pro(4OH)—2Nal—N((CH$_2$)$_2$OAc)(Bzl)

13

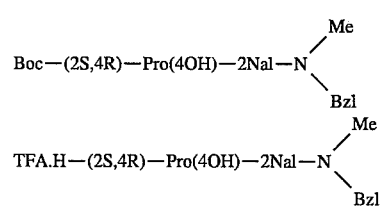

Boc—(2S,4R)—Pro(4OH)—2Nal—N(Me)(Bzl)

TFA.H—(2S,4R)—Pro(4OH)—2Nal—N(Me)(Bzl)

| Example No. | Formula |
|---|---|
| 1 | HCl.H—(2S,4R)—Pro(4OH)—2Nal—N(Me)(Bzl) |

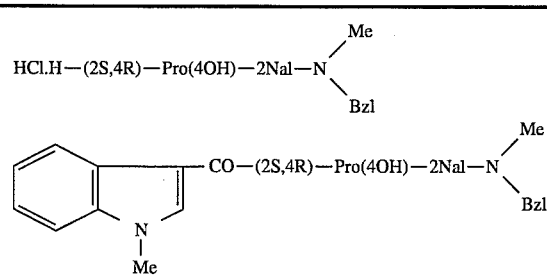

—CO—(2S,4R)—Pro(4OH)—2Nal—N(Me)(Bzl)

2-(1)

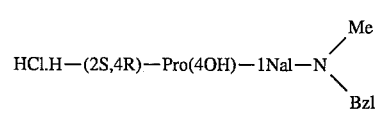

HCl.H—(2S,4R)—Pro(4OH)—1Nal—N(Me)(Bzl)

TABLE-continued
| | |
|---|---|
| | 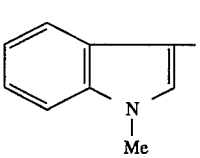—CO—(2S,4R)—Pro(4OH)—1Nal—N(Me)(Bzl) |
| 2-(2) | HCl.H—(2S,4R)—Pro(4OH)—2Nal—NHBzl |
| | 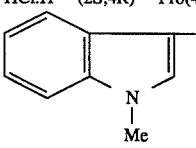—CO—(2S,4R)—Pro(4OH)—2Nal—NHBzl |
| 2-(3) | HCl.H—(2S,4R)—Pro(4OH)—2Nal—N(Me)((CH$_2$)$_2$Ph) |
| | 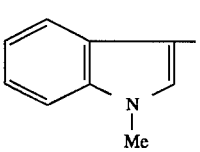—CO—(2S,4R)—Pro(4OH)—2Nal—N(Me)((CH$_2$)$_2$Ph) |
| 2-(4) | HCl.H—(2S,4R)—Pro(4OH)—2Nal—N(Me)(Bzl(m-F)) |
| | 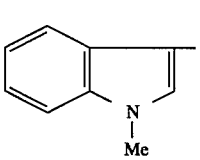—CO—(2S,4R)—Pro(4OH)—2Nal—N(Me)(Bzl(m-F)) |
| 2-(5) | HCl.H—(2S,4R)—Pro(4OH)—2Nal—N(Me)(Bzl(o-F)) |
| | 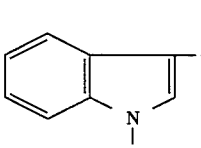—CO—(2S,4R)—Pro(4OH)—2Nal—N(Me)(Bzl(o-F)) |
| 2-(6) | HCl.H—(2S,4R)—Pro(4OH)—2Nal—NH(CH$_2$)$_2$Ph |
| | 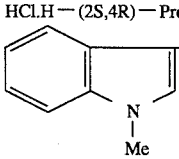—CO—(2S,4R)—Pro(4OH)—2Nal—NH(CH$_2$)$_2$Ph |
| 2-(7) | HCl.H—(2S,4R)—Pro(4OH)—2Nal—N((CH$_2$)$_2$OAc)(Bzl) |
| | 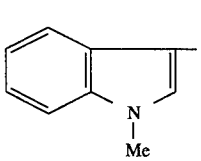—CO—(2S,4R)—Pro(4OH)—2Nal—N((CH$_2$)$_2$OAc)(Bzl) |

TABLE-continued
2-(8)
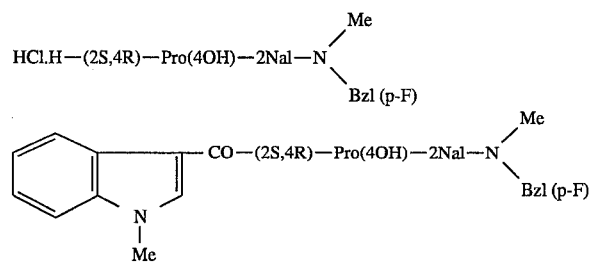
3
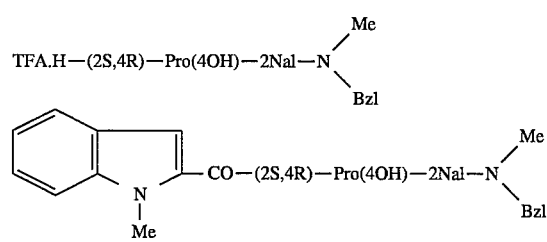
4-(1)
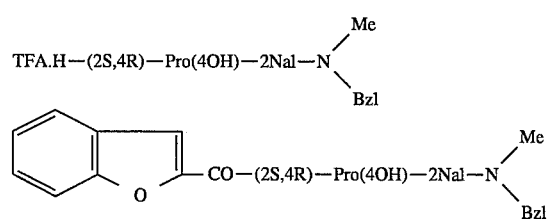
4-(2)
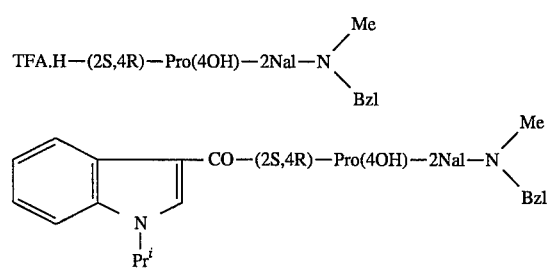
4-(3)
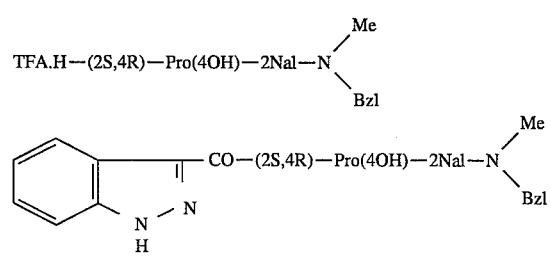
5
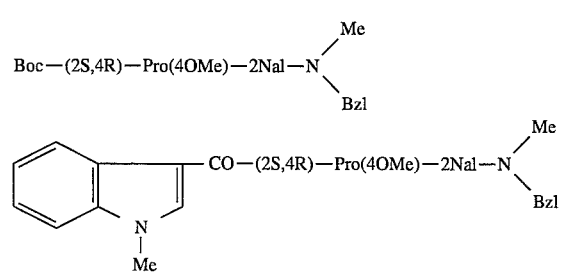
6
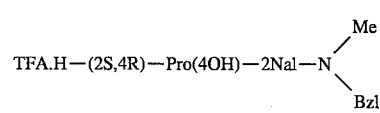

TABLE-continued

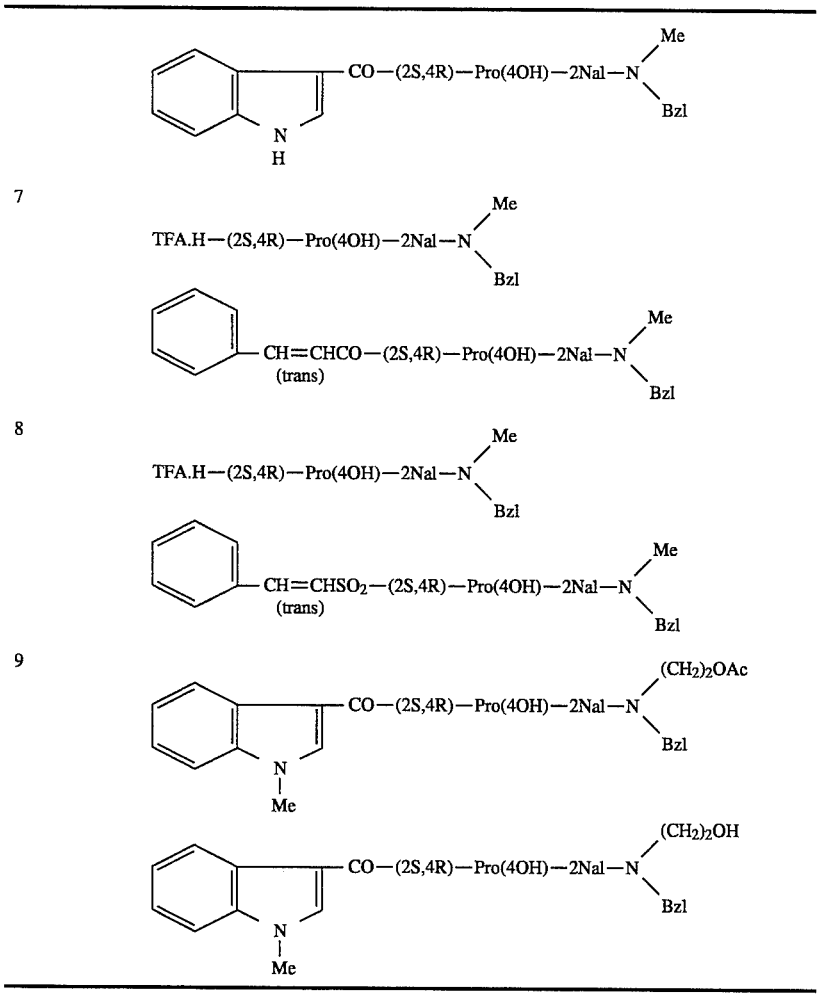

Preparation 1

To a suspended mixture of Starting Compound (2.0 g) in a mixed solvent of water (30 ml) and acetone (30 ml) was added triethylamine (1.94 ml) under ice-cooling. To the solution was added a solution of di-tert-butyldicarbonate (2.43 g) in acetone (10 ml), and the solution was stirred at the same temperature for two hours and at room temperature for additional two hours, during which period, di-tert-butyldicarbonate (0.4 g) was added. After removal of the acetone, water (50 ml) was added and the aqueous solution was washed once with ethyl acetate. The aqueous layer was then acidified to pH 2 with an addition of 6N hydrochloric acid and was extracted with ethyl acetate. The extract was washed with an aqueous sodium chloride solution and was dried over magnesium sulfate. After evaporation, the residue was crystallized from a mixture solvent of diisopropyl ether and n-hexane, and was collected by filtration and dried to give Object Compound (2.46 g).

mp: 91°–93° C. IR (Nujol): 3390, 1720, 1690, 1520, 1274, 1250, 1170 cm$^{-1}$ NMR (DMSO-d$_6$, δ): 1.28 (9H, s), 3.00 (1H, d of ABq, J=13.7 Hz and 10.1 Hz), 3.20 (1H, d, of ABq, J=13.7 Hz and 4.7 Hz), 4.20 (1H, m), 7.16 (1H, d, J=8.5 Hz), 7.4–7.6 (3H, m), 7.7–7.9 (1H, m)

Preparation 2

To an ice-cooled solution of Starting Compound (1.34 g), N-methylbenzylamine (0.49 ml), and HOBT (0.51 g) in methylene chloride (30 ml), was added WSC HCl (0.95 g). The solution was stirred at the same temperature for an hour and at room temperature overnight. After evaporation, the reaction mixture was extracted with ethyl acetate, and the organic layer was washed successively with water, and aqueous sodium hydrogencarbonate solution, 0.5N hydrochloric acid, water and an aqueous sodium chloride solution, and was dried over magnesium sulfate. Evaporation gave Object Compound (1.74 g) as an oil.

IR (CHCl$_3$): 3300, 1710, 1640, 1490, 1170 cm$^{-1}$ NMR (DMSO-d$_6$, δ): 1.22 and 1.32 (9H, s), 2.76 and 2.87 (3H, s), 2.9–3.2 (2H, m), 4.6–4.8 (3H, m), 6.9–8.0 (13H, m)

Preparation 3

To an ice-cooled solution of Starting Compound 1.74 g) in methylene chloride (17 ml) was added 4N-HCl/DOx (17 ml). The solution was stirred at the same temperature for five minutes. Then the cooling bath was removed and the solution was stirred at room temperature for half an hour, during which period 4N-HCl/DOX (8.4 ml) was added to the solution. After evaporation, the residue was triturated with diisopropyl ether, collected by filtration, and dried over sodium hydroxide in vacuo to give Object Compound (1.54 g).

mp: 141°–145° C. IR (Nujol): 3320, 2700, 1660, 1605, 1580, 1495, 1280 cm$^{-1}$ NMR (DMSO-d$_6$, δ): 2.65 and 2.71 (3H, s), 3.1–3.4 (2H, m), 4.09, 4.59 and 4.35, 4.56 (2H, two sets of ABq, J=16.2 Hz and 14.9 Hz respectively), 4.7–4.8 (1H, m), 7.0–7.25 (5H, m), 7.35–7.6 (3H, m), 7.8–8.0 (4H, m), 8.51 (3H, s)

Preparation 4

To an ice-cooled solution of Starting Compound (1.5 g), Boc-(2S,4R)-Pro(4OH)-OH (0.98 g) and HOBT (0.57 g) in a mixed solvent of methylene chloride (40 ml) and dimethylformamide (5 ml) was added WSC (0.77 ml). The solution was stirred at the same temperature for an hour and at room temperature overnight. After evaporation, the reaction mixture was extracted with ethyl acetate and the organic layer was washed successively with an aqueous sodium hydrogencarbonate solution, water, 0.5N hydrochloric acid, water and an aqueous sodium chloride solution, and was dried over magnesium sulfate. After evaporation, the residue was purified on a silica gel column (75 g) eluting with a mixed solvent of chloroform and methanol (50:1) to give Object Compound (1.74 g) as an amorphous solid.

IR ($CHCl_3$): 3320, 3250, 1690 (sh), 1680, 1640, 1500, 1160 $cm^{-1}$ NMR (DMSO-$d_6$, δ): 1.19 and 1.39 (9H, s), 1.75–2.05 (2H, m), 2.5–2.9 (3H, m), 3.0–3.5 (4H, m), 4.1–5.2 (6H, m), 6.95–7.3 (5H, m), 7.4–7.6 (3H, m), 7.75–7.95 (4H, m), 8.6–8.7 (1H, m)

Preparation 5

To an ice-cooled solution of Starting Compound (1.07 g) in methylene chloride (11 ml) was added 4N-HCl/DOX (8.2 ml). The solution was stirred at the same temperature for five minutes and at room temperature for fifty five minutes. After evaporation, the residue was triturated with diisopropyl ether, collected by filtration and dried to give Object Compound (0.90 g).

IR (Nujol): 3330, 2700, 1670 (sh), 1640, 1550 $cm^{-1}$ NMR (DMSO-$d_6$, δ) : 1.7–1.9 (1H, m), 2.2–2.4 (1H, m), 2.78 and 2.85 (3H, s), 3.0–3.4 (4H, m), 4.2–4.6 (4H, m), 5.0–5.2 (1H, m), 5.55–5.6 (1H, m), 6.9–8.0 (13H, m), 9.24 (1H, d, J=7.6 Hz)

Preparation 6

The object compound was obtained according to a similar manner to that of Preparation 1.

mp: 90°–91° C. IR (Nujol): 3370, 1730, 1660, 1400, 1250, 1165 $cm^{-1}$ NMR (DMSO-$d_6$, δ): 1.28 (9H, s), 3.20 (1H, dd, J=24.4 Hz and 10.4 Hz ), 3.59 (1H, dd, J=17.8 Hz and 3.9 Hz), 4.16–4.27 (1H, m), 7.26 (1H, d, J=8.4 Hz), 7.38–8.13 (7H, m), 12.75 (1H, br s)

Preparation 7

The object compounds were obtained according to a similar manner to that of Preparation 2.

(1) IR ($CHCl_3$) : 3310, 2995, 1705, 1640, 1490, 1365, 1250 $cm^{-1}$ NMR (DMSO-$d_6$, δ): 1.21 and 1.34 (9H, s), 2.53 and 2.71 (3H, s), 3.3–3.45 (2H, m), 4.2–4.55 (2H, m), 4.75–4.95 (1H, m), 6.95–8.2 (13H, m)

(2) mp: 161°–163° C. IR (Nujol): 3360, 1650, 1660, 1530, 1305, 1245, 1185 $cm^{-1}$ NMR (DMSO-$d_6$, δ): 1.28 (9H, s), 2.99 (1H, dd, J=13.1 Hz and 9.2 Hz), 3.14 (1H, dd, J=13.1 Hz and 5.5 Hz), 4.2–4.4 (3H, m), 7.05–7.25 (6H, m), 7.4–7.55 (3H, m), 7.7–7.9 (4H, m), 8.45 (1H, t, J=5.8 Hz) MASS: $M^{+1}$ 404

(3) IR ($CHCl_3$): 3450, 3310, 1705, 1635, 1605, 1365 $cm^{-1}$ NMR (DMSO-$d_6$, δ): 1.1–1.35 (9H, m), 2.55–3.0 (4H, m), 2.77 and 2.84 (3H, s), 3.2–3.7 (2H, m), 4.5–4.7 (1H, m), 7.05–7.95 (13H, m)

(4) IR ($CHCl_3$): 3320, 1705, 1640, 1595 $cm^{-1}$ NMR (DMSO-$d_6$, δ): 1.15–1.4 (9H, m), 2.75–3.2 (5H, m), 4.3–4.85 (3H, m), 6.8–7.65 (8H, m), 7.7–7.9 (4H, m)

(5) IR ($CHCl_3$): 3450, 3320, 1710, 1640, 1590, 1365 $cm^{-1}$ NMR (DMSO-$d_6$, δ): 1.1–1.4 (9H, m), 2.79 and 2.94 (3H, s), 2.8–3.15 (2H, m), 4.45–4.85 (1H, m), 6.8–7.6 (8H, m), 7.65–7.95 (4H, m)

(6) mp: 122°–123° C. IR (Nujol): 3350, 1690, 1650, 1525, 1320, 1270 $cm^{-1}$ NMR (DMSO-$d_6$, δ): 1.26 (9H, s), 2.66 (2H, t, J=7.0 Hz), 2.8–3.1 (2H, m), 3.2–3.4 (2H, m), 4.15–4.3 (1H, m), 6.92 (1H, d, J=8.48 Hz), 7.15–7.35 (5H, m), 7.4–7.5 (3H, m), 7.7–7.9 (4H, m), 7.95–8.1 (1H, m)

(7) IR ($CHCl_3$): 3470, 3330, 1710, 1645, 1610, 1370 $cm^{-1}$ NMR (DMSO-$d_6$, δ): 1.15–1.4 (9H, m), 2.7–3.2 (5H, m), 4.35–4.85 (3H, m), 6.85–8.0 (12H, m)

Preparation 8 starting Compound was dissolved in methylene chloride 35 ml and NMM (0.90 ml) was added to the solution. The solution was cooled to −22° C.—20° C. and isobutyl chloroformate (1.04 ml) dissolved in methylene chloride (2 ml) was added dropwise thereto at the same temperature. The solution was stirred for a quarter an hour during which period the temperature was maintained at −25° C.~ −20° C. Then the solution was cooled to −30° C. and N-benzyl ethanolamine (1.21 g) dissolved in methylene chloride (3 ml) was added at a time. The solution was stirred for two hours, during which period the temperature was raised to 20° C. After concentration, the residue was extracted with ethyl acetate and the organic layer was successively washed with water, sodium hydrogencarbonate solution, water, 0.5N hydrochloric acid, and sodium chloride solution, and was dried over magnesium sulfate. After concentration, the crude product was purified on a column of silica gel (50 g) eluting first with chloroform and with a mixed solvent of chloroform and methanol (1.5%) to give Object Compound (2.69 g).

IR ($CHCl_3$): 3430, 3300, 1700, 1630 $cm^{-1}$ MASS: (m/e) 448

Preparation 9

To a solution of Starting Compound (2.65 g) and pyridine (4.67 g) in THF (50 ml) was added acetyl chloride (0.928 g) under ice-cooling. After the addition, the mixture was stirred for an hour at the same temperature. After concentration, the residue was extracted with ethyl acetate and the organic layer was successively washed with water, 0.5N hydrochloric acid, sodium hydrogencarbonate solution, and sodium chloride solution, and dried over magnesium sulfate. Concentration gave Object Compound (2.82 g) as an oil.

IR ($CHCl_3$): 3330, 1742, 1710, 1640 $cm^{-1}$

Preparation 10

The object compounds were obtained according to a similar manner to that of Preparation 3.

(1) IR (Nujol): 3495, 1645, 1625, 1510, 1495, 1265 $cm^{-1}$ NMR (DMSO-$d_6$, δ): 3.2–3.45 (1H, m), 3.36 (3H, s), 3.87 (1H, dd, J=8.6 Hz and 4.3 Hz), 4.28 (2H, s), 4.64 (1H, dd, J=7.4 Hz and 4.4 Hz), 6.75–8.15 (12H, m), 8.73 (2H, br s)

(2) mp: 183°–185° C. IR (Nujol): 3430, 1675, 1600, 1575, 1545, 1250, 1160, $cm^{-1}$ NMR (DMSO-$d_6$, δ): 3.26 (2H, d, J=7.1 Hz), 4.1–4.25 (2H, m), 4.36 (1H, dd, J=15.1 Hz and 6.4 Hz), 6.9–7.2 (5H, m), 7.4–7.6 (3H, m), 7.7–7.95 (4H, m), 8.48 (3H, br s), 9.05 (1H, t, J=5.7 Hz)

(3) IR ($CHCl_3$): 3500–3350, 1650, 1600, 1500 $cm^{-1}$ NMR (DMSO-$d_6$, δ): 2.3–2.8 (5H, m), 3.05–3.70 (4H, m), 4.55–4.7 (1H, m), 7.1–7.6 and 7.7–8.0 (12H, m), 8.42 (3H, br s)

(4) IR ($CHCl_3$): 3420, 1785, 1655, 1640, 1620, 1595 $cm^{-1}$ NMR (DMSO-$d_6$, δ): 2.67 and 2.71 (3H, s), 3.15–3.4 (2H, m), 4.05–4.85 (3H, m), 6.8–8.0 (11H, m), 8.51 (3H, br s)

(5) IR ($CHCl_3$): 3500–3350, 1785, 1655–1645, 1600, 1585, 1370 $cm^{-1}$ NMR (DMSO-$d_6$, δ): 2.71 (3H, s), 3.1–3.4 (2H, m), 4.1–4.9 (3H, m), 6.85–8.0 (11H, m), 8.52 (3H, br s)

(6) IR ($CHCt_3$): 3450–3150, 1665, 1600, 1455, 1370, 1120 $cm^{-1}$ NMR (DMSO-$d_6$, δ): 2.45–2.7 (2H, m), 3.1–3.5 (4H, m), 4.07 (1H, t, J=6.7 Hz), 7.05–7.6 (8H, m), 7.7–7.95 (4H, m), 8.38 (3H, br s), 8.7–8.8 (1H, m)

(7) mp: 145° C. (dec.) IR (Nujol): 3450, 1650, 1605, 1510, 1285, 1225 cm$^{-1}$ NMR (DMSO-d$_6$, δ): 2.64 and 2.69 (3H, s), 3.1–3.4 (2H, m), 4.05–4.85 (3H, m), 6.85–7.1 and 7.35–8.0 (11H, m), 8.53 (3H, br s)

(8) IR (CHCl$_3$): 3450–3370, 1740, 1650, 1600, 1365 cm$^{-1}$ NMR (DMSO-d$_6$, δ): 1.89 and 1.96 (3H, s), 3.0–3.8 (6H, m), 3.9–4.9 (3H, m), 7.0–7.6 (8H, m), 7.7–8.0 (4H, m), 8.55 (2H, br s)

Preparation 11

The object compounds were obtained according to a similar manner to that of Preparation 4.

(1) IR (Neat): 3300, 1690, 1640 cm$^{-1}$ NMR (DMSO-d$_6$, δ): 1.18 (s) and 1.39 (s)(9H), 1.5–1.8 (1H, m), 1.9–2.3 (1H, m), 2.7–2.9 (3H, m), 2.9–3.3 (2H, m), 3.3–3.5 (2H, m), 3.7–3.9 (1H, m), 4.0–5.2 (4H, m), 6.8–7.3 (5H, m), 7.3–7.6 (3H, m), 7.6–7.9 (4H, m), 8.4–8.5 (1H, m)

(2) IR (CHCl$_3$): 3420, 3300, 1680, 1630, 1520, 1490, 1400 cm$^{-1}$ NMR (DMSO-d$_6$, d): 1.32 and 1.41 (9H, s), 1.6–1.8 (1H, m), 1.8–2.0 (1H, m), 2.44 and 2.66 and 2.74 (3H, m), 3.2–3.5 (4H, m), 4.15–4.60 and 4.9–5.3 (6H, m), 6.70–8.60 (13H, m)

(3) mp: 205° C. (dec.). IR (Nujol): 3400, 3350, 3280, 3100, 1680, 1645, 1570, 1540, 1290, 1170 cm$^{-1}$ NMR (DMSO-d$_6$, δ): 1.08 and 1.34 (9H, s), 1.5–1.8 (1H, m), 1.8–2.05 (1H, m), 2.95–3.5 (4H, m), 4.05–4.4 and 4.45–4.8 and 4.9–5.0 (6H, m), 7.0–7.25 (5H, m), 7.35–7.5 (3H, m), 7.7–7.9 (4H, m), 8.1–8.3 (1H, m), 8.5–8.6 (1H, m) MASS: M$^{+1}$ 517

(4) IR (CHCl$_3$): 3420, 3300, 1690–1670, 1630, 1370 cm$^{-1}$ NMR (DMSO-d$_6$, δ): 1.1–1.25 and 1.3–1.5 (9H, m), 1.55–1.75 (1H, m), 1.75–2.0 (1H, m), 2.5–3.1 and 3.2–3.8 (11H, m), 4.0–4.25 (2H, m), 4.9–5.05 (2H, m), 7.05–7.6 and 7.6–7.9 (12H, m), 8.2–8.4 (1H, m)

(5) IR (CHCl$_3$): 3450–3250, 1700–1655, 1645, 1595 cm$^{-1}$ NMR (DMSO-d$_6$, δ): 1.1–1.4 (9H, m), 1.55–1.75 (1H, m), 1.8–2.0 (1H, m), 2.7–3.5 (7H, m), 4.1–5.2 (6H, m), 6.7–7.3 and 7.4–7.6 and 7.7–7.9 (11H, m), 8.4–8.5 (1H, m)

(6) IR (CHCl$_3$): 3450–3300, 1690–1630, 1640, 1370, 1160 cm$^{-1}$ NMR (DMSO-d$_6$, δ): 1.1–1.45 (9H, m), 1.6–1.8 (1H, m), 1.85–2.05 (1H, m), 2.7–3.5 (7H, m), 4.1–4.7 and 4.9–5.2 (6H, m), 6.7–7.9 (11H, m), 8.35–8.5 (1H, m)

(7) mp: 202°–203° C. IR (Nujol): 3360, 3270, 3070, 1665, 1635, 1535, 1420, 1285, 1170 cm$^{-1}$ NMR (DMSO-d$_6$, δ): 1.07 and 1.40 (9H, s), 1.5–1.75 (1H, m), 1.8–2.0 (1H, m), 2.55–2.7 (2H, m), 2.9–3.4 (6H, m), 4.0–4.2 and 4.25–4.65 (3H, m), 4.93 (1H, dd, J=9.78 Hz and 6.43 Hz), 7.1–7.55 and 7.65–8.2 (14H, m)

(8) IR (CHCl$_3$): 3450–3300, 1690–1670, 1640, 1370, 1160 cm$^{-1}$ NMR (DMSO-d$_6$, δ): 1.0–1.5 (9H, m), 1.6–1.8 (1H, m), 1.85–2.05 (1H, m), 2.7–2.9 (3H, m), 3.0–3.5 (4H, m), 4.1–5.2 (6H, m), 6.8–7.05 and 7.4–7.95 (11H, m), 8.35–8.5 (1H, m)

(9) IR (CHCl$_3$): 3450–3430, 1740, 1695–1680, 1365, 1160 cm$^{-1}$ (DMSO-d$_6$, δ): 1.1–1.5 (9H, m), 1.5–1.75 (1H, m), 1.8–2.0 (4H, m), 2.9–3.9 (8H, m), 3.9–5.2 (6H, m), 6.95–8.0 (12H, m), 8.4–8.5 (1H, m)

Preparation 12

The object compounds were obtained according to a similar manner to that of Preparation 5.

(1) IR (CHCl$_3$): 3350–3200, 3050, 1685, 1645–1630, 1550, 1495, 1450 cm$^{-1}$ NMR (DMSO-d$_6$, δ): 1.60–1.90 (1H, m), 2.15–2.40 (1H, m), 2.39 and 2.69 (3H, m), 3.0–3.6 (4H, m), 4.1–4.5 and 5.1–6.75 (6H, m), 6.9–8.35 and 9.3–9.4 (12H, m), 8.71 (1H, br s), 10.18 (1H, br s)

(2) mp 250° C. (dec.) IR (Nujol): 3300, 2700, 1665, 1650, 1560, 1295, 1255 cm$^{-1}$ NMR (DMSO-d$_6$, δ): 1.75–1.95 (1H, m), 2.25–2.4 (1H, m), 3.0–3.5 (4H, m), 4.15–4.45 (4H, m), 4.65–4.8 (1H, m), 5.52 (1H, br s), 7.0–7.2 (5H, m), 7.45–7.55 (3H, m), 7.75–7.9 (4H, m), 8.56 (1H, br s), 8.74 (1H, t, J=5.9 Hz), 9.04 (1H, d, J=8.1 Hz ), 9.83 (1H, br s )

(3) IR (CHCl$_3$): 3400–3200, 1680, 1630 cm$^{-1}$ NMR (DMSO-d$_6$, δ): 1.7–1.9 (1H, m), 2.2–2.4 (1H, m), 2.5–2.75 (2H, m), 2.79 and 2.83 (3H, s), 2.95–3.2 and 3.2–4.7 (6H, m), 4.2–4.45 and 4.9–5.1 (4H, m), 7.05–7.55 and 7.65–8.0 (12H, m), 8.6 (1H, br s), 9.1–9.25 (1H, m), 9.97 (1H, br s)

(4) IR (CHCl$_3$): 3400–3200, 1680, 1640, 1590 cm$^{-1}$ NMR (DMSO-d$_6$, δ): 1.7–1.9 (1H, m), 2.2–2.4 (1H, m), 2.78 and 2.88 (3H, m), 3.0–3.4 (4H, m), 4.2–4.75 and 5.0–5.2 and 5.5–5.7 (6H, m), 6.8–7.95 (11H, m), 8.6 (1H, br s), 9.26 (1H, d, J=7.6 Hz), 9.95 (1H, br s)

(5) IR (CHCl$_3$): 3350–3200, 1680, 1640, 1550 cm$^{-1}$ NMR (DMSO-d$_6$, δ): 1.7–1.9 (1H, m), 2.2–2.4 (1H, m), 2.8 and 2.92 (3H, s), 3.0–3.5 (4H, m), 4.2–4.85 and 5.0–5.2 (6H, m), 6.7–7.95 (11H, m), 8.6 (1H, br s), 9.26 (1H, d, J=7.72 Hz), 10.05 (1H, br s)

(6) mp: 259°–261° C. IR (Nujol): 3300, 2700, 1670, 1645, 1555, 1290, 1250 cm$^{-1}$ NMR (DMSO-d$_6$, δ): 1.7–1.9 (1H, m), 2.25–2.4 (1H, m), 2.65 (2H, t, J=7.12 Hz), 2.9–3.45 (6H, m), 4.2–4.7 (3H, m), 5.54 (1H, d, J=2.91 Hz), 7.1–7.55 and 7.7–7.9 (12H, m), 8.5–8.7 (2H, m), 8.97 (1H, d, J=8.24 Hz), 9.9 (1H, s)

(7) IR (CHCl$_3$): 3400–3220, 1680, 1640, 1610, 1225 cm$^{-1}$ NMR (DMSO-d$_6$, δ): 1.75–1.9 (1H, m), 2.2–2.4 (1H, m), 2.75 and 2.84 (3H, s), 3.0–3.4 (4H, m), 4.2–4.65 and 5.1–5.7 (6H, m), 6.8–7.1 and 7.3–7.95 (11H, m), 8.62 (1H, br s), 9.25 (1H, d, J=7.47 Hz), 9.93 (1H, br s)

(8) IR (CHCl$_3$): 3320–3180, 1740, 1685, 1640, 1365 cm$^{-1}$ NMR (DMSO-d$_6$, δ): 1.7–2.0 (4H, m), 2.1–2.4 (1H, m), 3.0–3.7 and 4.0–4.2 (8H, m), 4.25–5.7 (6H, m), 7.0–8.0 (12H, m), 8.6 (1H, br s), 9.2–9.35 (1H, m), 9.94 (1H, br s)

Preparation 13

To a solution of Starting Compound (10.0 g) in methylene chloride (20 ml), was added trifluoroacetic acid (50 ml) under ice-cooling. The solution was stirred for half an hour at the same temperature and was evaporated under vacuum. The residue was crystallized by adding ether (50 ml) and filtered, washed with ether, and dried to give Object Compound (9.26 g).

mp: 157°–159° C. IR (Nujol): 3400, 3330, 3150, 1670, 1625, 1565, 1495, 1200 cm$^{-1}$ NMR (DMSO-d$_6$, δ): 1.7–1.95 (1H, m), 2.2–2.45 (1H, m), 2.79 and 2.87 (3H, s), 3.0–3.4 (4H, m), 4.2–4.7 and 5.0–5.15 (6H, m), 6.9–8.0 and 9.15–9.3 (12H, m), 8.65 (1H, br s), 9.71 (1H, br s)

EXAMPLE 1

To an ice-cooled solution of 1-methylindole-3-carboxylic acid (0.33 g), Starting Compound (0.88 g) and HOBT (0.25 g) was added WSC (0.34 ml). The solution was stirred at the same temperature for an hour and at room temperature overnight. After evaporation, the reaction mixture was extracted with ethyl acetate and the organic layer was washed successively with an aqueous sodium hydrogencarbonate solution, water, 0.5N hydrochloric acid, water, and an aqueous sodium chloride solution, and dried over magnesium sulfate. After evaporation, the residue was purified on a silica gel column (50 g) eluting with a mixed solvent of chloroform and methanol (50:1). The fractions containing the desired compound were collected and evaporated. The residue was then crystallized from ethyl acetate, collected by filtration and dried to give Object Compound (0.66 g).

mp: >115° C. (dec.) IR (Nujol): 3430, 3300, 1656, 1640, 1600, 1574, 1535 cm$^{-1}$ NMR (DMSO-d$_6$, δ): 1.7–2.2 (2H, m), 2.71 and 2.80 (3H, s), 3.0–3.25 (2H, m), 3.6–3.7 (1H, m), 3.85 (3H, s), 3.8–4.0 (1H, m), 4.2–4.55 (3H, m), 4.65–4.8 (1H, m), 5.0–5.2 (2H, m), 6.9–7.3 (7H, m), 7.4–7.55 (4H, m), 7.7–7.9 (5H, m), 8.08 (1H, d, J=7.4 Hz), 8.5–8.6 (1H, m) Elemental Analysis Calculated for $C_{36}H_{36}N_4O_4 \cdot H_2O$: C 72.27, H 6.31, N 9.23 Found: C 72.17, H 6.42, N 9.04

EXAMPLE 2

The object compounds were obtained according to a similar manner to that of Example 1.

(1) IR (CHCl$_3$): 3450–3300, 3005, 1645, 1630, 1595, 1530, 1470, 1370 cm$^{-1}$ NMR (DMSO-d$_6$, δ): 1.6–1.9 (1H, m), 1.9–2.15 (1H, m), 2.42 and 2.63 (3H, s), 3.35–4.0 (4H, m), 3.87 (3H, s), 4.2–4.4 (3H, m), 4.6–5.3 (3H, m), 6.7–8.15 (17H, m), 8.54 (1H, br s)

(2) mp: 213°–215° C. IR (Nujol): 3280, 1660, 1635, 1590, 1570, 1535, 1340, 1250, 1255 cm$^{-1}$ NMR (DMSO-d$_6$, δ): 1.65–1.85 (1H, m), 1.85–2.05 (1H, m), 3.0–3.4 (2H, m), 3.6–4.4 (5H, m), 3.86 (3H, s), 4.5–4.7 (2H, m), 5.04 (1H, d, J=3.3 Hz), 7.0–7.3 (7H, m), 7.3–7.6 (4H, m), 7.7–8.0 (5H, m), 8.09 (1H, d, J=7.7 Hz), 8.2–8.45 (2H, m)

(3) mp: 130°–134° C. IR (Nujol): 3400, 3270, 3070, 1650, 1630, 1600, 1565, 1535, 1320 cm$^{-1}$ NMR (DMSO-d$_6$, δ): 1.7–1.9 (1H, m), 1.9–2.1 (1H, m), 2.5–2.7 (2H, m), 2.72 and 2.78 (3H, s), 2.9–3.7 (6H, m), 3.84 (3H, m), 4.15–4.3 (1H, m), 4.6–4.8 (1H, m), 4.95–5.05 (1H, m), 7.0–7.55 (11H, m), 7.75–7.9 (5H, m), 8.0–8.1 (1H, m), 8.3–8.5 (1H, m)

(4) mp: 129° C. (dec.) IR (Nujol): 3420, 3290, 3060, 1655, 1625, 1600, 1560, 1535, 1320 cm$^{-1}$ NMR (DMSO-d$_6$, δ): 1.7–1.9 (1H, m), 1.9–2.1 (1H, m), 2.71 and 2.82 (3H, s), 3.0–3.4 (2H, m), 3.6–3.7 (1H, m), 3.85 (3H, s), 3.8–4.0 (1H, m), 4.2–5.2 (6H, m), 6.8–8.1 (16H, m), 8.5–8.6 (1H, m)

(5) mp: 134°14 136° C. IR (Nujol): 3380, 3060, 1685, 1655, 1590, 1545, 1335, 1250 cm$^{-1}$ NMR (DMSO-d$_6$, δ): 1.7–1.9 (1H, m), 1.9–2.1 (1H, m), 2.72 and 2.87 (3H, s), 3.1–3.45 (2H, m), 3.6–3.75 (1H, m), 3.8–4.0 (1H, m), 3.85 (3H, s), 4.2–5.2 (6H, m), 6.8–8.2 (16H, m), 8.53 (1H, br s)

(6) mp: 195°–197° C. IR (Nujol): 3350, 3270, 3100, 1660, 1630, 1590, 1570, 1535, 1310, 1245 cm$^{-1}$ NMR (DMSO-d 6): 1.65–1.85 (1H, m), 1.85–2.0 (1H, m), 2.45–2.6 (2H, m), 3.0–3.35 (4H, m), 3.65–4.1 (2H, m), 3.88 (3H, s), 4.25–4.6 (3H, m), 5.05 (1H, d, J=3.13 Hz), 7.0–7.6 (11H, m), 7.45–8.05 (6H, m), 8.15–8.25 (2H, m)

(7) IR (CHCl$_3$): 3450–3320, 1745, 1650–1635, 1375 cm$^{-1}$ NMR (DMSO-d$_6$, δ): 1.7–1.9 (4H, m), 1.9–2.1 (1H, m), 3.0–4.1 (11H, m), 4.2–5.2 (6H, m), 6.9–7.95 (16H, m), 8.0–8.15 (1H, m), 8.5–8.65 (1H, m)

(8) mp: 105° C. (dec.) IR (Nujol): 3450, 3270, 1665, 1640, 1605, 1575, 1535, 1510, 1245 cm$^{-1}$ NMR (DMSO-d$_6$, δ): 1.7–1.9 (1H, m), 1.9–2.1 (1H, m), 2.68 and 2.80 (3H, m), 3.0–3.3 (2H, m), 3.6–4.0 (2H, m), 3.86 (3H, s), 4.2–5.15 (6H, m), 6.65–8.15 (16H, m), 8.4–8.6 (1H, m)

EXAMPLE 3

To a suspended mixture of 1-methylindole-2-carboxylic acid (225 mg) and HOBT (173 mg) in methylene chloride (10 ml) was added WSC.HCl (246 mg) at room temperature. The solution was stirred at the same temperature for an hour.

In another reaction vessel, Starting Compound (700 mg) was dissolved in methylene chloride (10 ml), and TEA (0.20 ml) was added to the solution under ice-cooling. After the solution was stirred at room temperature for quarter an hour, the above solution was added to it. The solution was stirred for six hours, and TEA (0.05 ml) was added to the solution and was stirred overnight. After concentration, the residue was extracted with ethyl acetate, the organic layer was washed successively with saturated sodium hydrogencarbonate solution, water, 0.5N hydrochloric acid, and sodium chloride solution, and dried over magnesium sulfate. After concentration, the residue was crystallized by addition of acetone, filtered, washed with acetone, and dried at 40° C. under vacuum to give Object Compound (0.47 g).

mp: 183.0°–184.0° C. IR (Nujol): 3350, 3275, 3110, 1670, 1640, 1577, 1530, 1495, 1465, 1355, 1340, 1318, 813, 735, 693 cm$^{-1}$ NMR (DMSO-d$_6$, δ): 1.65–2.20 (2H, m), 2.730, 2.822 (3H, s), 3.00–3.40 (2H, m), 3.50–3.95 (2H, m), 3.756, 3.827 (3H, s), 4.05–5.20 (6H, m), 6.05–7.90 (17H, m), 8.50–8.65 (1H, m) Elemental Analysis Calculated for $C_{36}H_{36}N_4O_4$: C 73.45, H 6.16, N 9.52 Found: C 73.44, H 6.17, N 9.50

EXAMPLE 4

The object compounds were obtained according to a similar manner to that of Example 3.

(1) IR (CHCl$_3$): 3300, 3000, 1630, 1560, 1450, 1420 cm$^{-1}$ NMR (DMSO-d$_6$, δ): 1.7–1.9 (1H, m), 2.2–2.4 (1H, m), 2.6–2.8 (3H, m), 3.0–3.3 (2H, m), 3.36 (1H, m), 3.67 (1H, m), 3.8–5.2 (6H, m), 6.8–7.9 (17H, m), 8.65–8.85 (1H, m)

(2) mp: 111°–114° C. IR (Nujol): 3420, 3280, 1655, 1630, 1600, 1530, 1225 cm$^{-1}$ NMR (DMSO-d$_6$, δ): 1.51 (6H, br s), 1.7–2.1 (2H, m), 2.7–2.9 (3H, m), 3.0–3.3 (2H, m), 3.6–3.75 (1H, m), 3.9–4.1 (1H, m), 4.2–4.55 (3H, m), 4.7–5.2 (4H, m), 6.9–7.3 (7H, m), 7.4–7.95 (9H, m), 8.07 (1H, m), 8.55 (1H, m) Elemental Analysis Calculated for $C_{38}H_{40}N_4O_4$: C 74.00, H 6.54, N 9.08 Found: C 73.53, H 6.48, N 8.95

(3) mp: 219°–222° C. IR (Nujol): 3460, 3250, 3100, 1678, 1640, 1570 cm$^{-1}$ NMR (DMSO-d$_6$, δ): 1.8–2.1 (2H, m), 2.6–2.9 (3H, m), 3.1–3.3 (2H, m), 3.7–4.2 (2H, m), 4.2–4.8 (3H, m), 5.0–5.4 (3H, m), 6.7–7.9 (15H, m), 8.2 (1H, m), 8.65 (1H, m), 13.6 (1H, br s)

EXAMPLE 5

The object compound was obtained according to similar manners to those of Preparation 5 and Example 1 successively.

IR (Nujol): 3300, 1635, 1610, 1535 cm$^{-1}$ NMR (DMSO-d$_6$, δ): 1.7–2.0 (1H, m), 2.0–2.3 (1H, m), 2.71 (s) and 2.81 (s) (3H), 2.9–3.3 (2H, m), 3.13 (s) and 3.15 (s)(3H), 3.7–4.0 (6H, m), 4.3–4.7 (3H, m), 4.9–5.2 (1H, m), 6.8–7.3 (7H, m), 7.3–7.6 (4H, m), 7.6–8.0 (5H, m), 8.0–8.1 (1H, m), 8.4–8.7 (1H, m)

EXAMPLE 6

To an ice-cooling solution of Starting Compound (0.5 g) in methylene chloride (15 ml) was added successively BSA (0.68 ml) and indole-3-carbonyl chloride (0.20 g). The solution was stirred at the same temperature for an hour, during which period indole-3-carbonyl chloride in three portions (0.20 g, 0.08 g and 0.20 g) and BSA (0.3 ml) were added to the solution. After concentration, the residue was dissolved in THF (10 ml), and 1N-hydrochloric acid (1 ml) was added under ice-cooling. The solution was stirred at the same temperature for 15 minutes. After concentration, the residue was extracted with ethyl acetate. The organic layer was washed successively with an aqueous sodium hydrogencarbonate solution and saturated sodium chloride solution, dried over magnesium sulfate, and concentrated in vacuo. The residue was purified by column chromatography on silica gel eluting first with ethyl acetate and then with a mixed solution of chloroform, methanol and ethyl acetate (4:1:1) to give Object Compound as an amorphous solid (0.28 g).

IR (Nujol): 3275, 1630, 1530 cm$^{-1}$ NMR (DMSO-d$_6$, δ): 1.65–2.00 (2H, m), 2.708, 2809 (3H, s), 3.00–3.25 (2H, m), 3.60–4.00 (2H, m), 4.20–5.20 (6H, m), 6.80–8.10 (17H, m), 8.40–8.60 (1H, br s), 11.60 (1H, s)

EXAMPLE 7

To a suspended mixture of Starting Compound (1.0 g) in methylene chloride (20 ml) was added TEA (0.51 ml) and cinnamoyl chloride (0.31 g) under ice-cooling. The solution was stirred at the same temperature for three hours and at room temperature overnight. After evaporation, the reaction mixture was extracted with ethyl acetate and the organic layer was washed successively with an aqueous sodium hydrogencarbonate solution, water, 0.5N hydrochloric acid, water, and an aqueous sodium chloride solution, and dried over magnesium sulfate. After evaporation, the residue was purified on a silica gel column (50 g) eluting with a mixed solvent of chloroform and methanol (40:1). The fractions containing the desired compound were collected and evaporated. The residue was then crystallized from isopropyl ether, collected by filtration and dried to give Object Compound (0.66 g).

IR (CHCl$_3$): 3400, 3300, 3000, 1640, 1600, 1545, 1495, 1450, 1420 cm$^{-1}$ NMR (DMSO-d$_6$, δ): 1.6–2.3 (2H, m), 2.6–2.9 (3H, m), 2.9–3.3 (2H, m), 3.5–3.9 (2H, m), 4.2–5.2 (6H, m), 6.65–7.9 (19H, m), 8.45–8.6 and 8.9–9.05 (1H, m)

EXAMPLE 8

The object compound was obtained according to a similar manner to that of Example 7.

IR (CHCl$_3$): 3400, 1635, 1510, 1490, 1450, 1340, 1145 cm$^{-1}$ NMR (DMSO-d$_6$, δ): 1.6–1.8 (1H, m), 1.8–2.0 (1H, m), 2.77 and 2.86 (3H, s), 3.0–3.35 (3H, m), 3.45–3.65 (1H, m), 4.1–4.7 and 4.95–5.2 (6H, m), 6.95–7.9 (19H, m), 8.4–8.55 (1H, m)

EXAMPLE 9

To an ice-cooled solution of Starting Compound (0.72 g) in methanol (15 ml) was added 1N sodium hydroxide (1.1 ml) solution. The solution was stirred for 3 hours at room temperature. After concentration, the product was extracted with ethyl acetate and the organic layer was washed successively with water and sodium chloride solution, and was dried over magnesium sulfate. After evaporation of the solvent, the solid residue was washed with ethyl acetate, filtered and dried to give Object Compound (0.60 g).

mp: 115° C. (dec.) IR (Nujol): 3470, 3290, 1665, 1620, 1605, 1575, 1535, 1250 cm$^{-1}$

What we claim is:
1. A compound of the formula

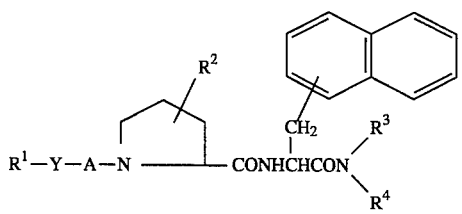

wherein
$R^1$ is phenyl, benzofuryl, indazolyl, indolyl or 1-lower alkylindolyl,
$R^2$ is hydroxy or lower alkoxy,
$R^3$ is lower alkyl,
$R^4$ is phenyl(lower)alkyl or halophenyl(lower)alkyl,
A is carbonyl and
Y is a bond or lower alkenylene,
and a pharmaceutically acceptable salt thereof.

2. A compound of claim 1, wherein
$R^1$ is benzofuryl, indazolyl, indolyl or 1-lower alkylindolyl,
A is carbonyl, and
Y is bond.

3. A compound of claim 2, wherein
$R^1$ is benzofuryl, indazolyl, indolyl, 1-methylindolyl or 1-isopropylindolyl,
$R^2$ is hydroxy or methoxy,
$R^3$ is hydrogen, methyl, hydroxyethyl or acetoxyethyl,
$R^4$ is benzyl, phenethyl, o-fluorobenzyl, m-fluorobenzyl or p-fluorobenzyl.

4. A compound of claim 3, which is selected from the group consisting of:

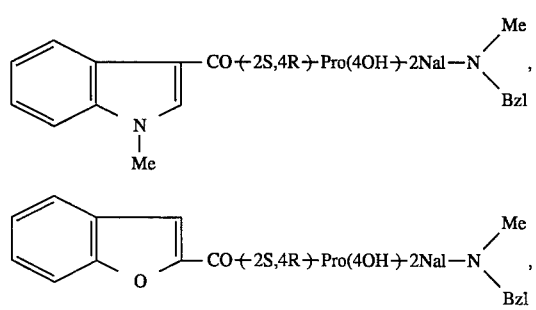

and

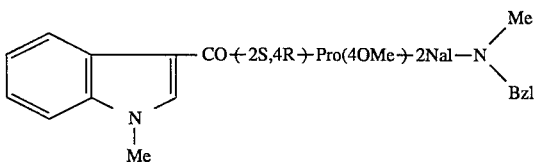

5. A compound of claim 1, wherein
$R^1$ is phenyl,
A is carbonyl or sulfonyl, and
Y is lower alkenylene.

6. A compound of claim 5, wherein
$R^2$ is hydroxy, $R^3$ is methyl,
$R^4$ is benzyl, and
Y is vinylene.

7. A compound of claim 6, which is selected from the group consisting of:

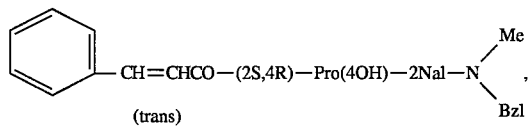
(trans)

and

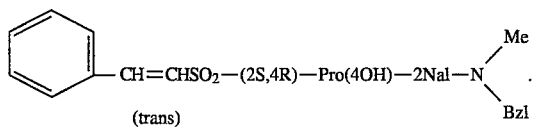
(trans)

8. A pharmaceutical composition which comprise a compound of claim 1 and a pharmaceutically acceptable carrier or excipient.

9. A process for preparing a pharmaceutical composition which comprises admixing a compound of claim 1 with a pharmaceutically acceptable carrier or excipient.

10. A method for treating bronchoedema which comprises administering an effective amount of a compound of claim 1 to a subject in need thereof.

* * * * *